(12) United States Patent
Kobayashi et al.

(10) Patent No.: US 6,338,946 B1
(45) Date of Patent: Jan. 15, 2002

(54) METHOD FOR ASSAYING IMMUNOSUPPRESSANT

(75) Inventors: Masakazu Kobayashi, Takarazuka; Kouichi Tamura, Kobe, both of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/457,395

(22) Filed: Dec. 9, 1999

Related U.S. Application Data

(63) Continuation of application No. 08/702,549, filed on Oct. 24, 1996, now abandoned, and a continuation of application No. PCT/JP95/00372, filed on Mar. 8, 1995.

(30) Foreign Application Priority Data

Mar. 10, 1994 (JP) ................................................ 6/39534

(51) Int. Cl.$^7$ ........................ G01N 33/53; G01N 33/567; A61K 38/00; C07K 1/00
(52) U.S. Cl. ..................... 435/7.1; 435/7.21; 435/7.8; 435/7.92; 514/11; 514/15; 530/402
(58) Field of Search .......................... 435/7.1, 7.2, 7.8, 435/7.92; 514/11, 15; 530/402

(56) References Cited

U.S. PATENT DOCUMENTS

| 5,362,629 A | 11/1994 | Schreiber et al. ............. 435/21 |
| 5,457,182 A | 10/1995 | Wiederrecht et al. ....... 530/402 |
| 5,639,852 A | 6/1997 | Rich et al. .................. 530/317 |

OTHER PUBLICATIONS

K. Tamura et al., "Interaction of Tacrolimus(FK506) and Its Metabolites with FKBP and Calcineurin", Biochemical and Biophysical Research Communications, vol. 202, No. 1, pp. 437–443, 1994.

Jun Liu et al., "Calcineurin in a Common Target of Cyclophilin–Cyclosporin A and FKBP–FK506 Complexes", Cell, vol. 66, pp. 807–815, Aug. 23, 1991.

Alice Haddy et al., "Inhibition of Calcineurin by Cyclosporin A–Cyclophilin Requires Calcineurin B", FEBS 11823, vol. 314, No. 1, pp. 37–40, Dec. 1992.

Masako Asami et al., "Detection of the FK506–FKBP–Calcineurin Complex by a Simple Binding Assay", Biochemical and Biophysical Research Communications, vol. 192, No. 3, pp. 1388–1394, 1993.

Primary Examiner—Jezia Riley
(74) Attorney, Agent, or Firm—Oblon, Spivak, McClelland, Maier & Neustadt, P.C.

(57) ABSTRACT

This invention relates to a method and kit for assaying an immunosuppressant having a calcineurin-inhibiting activity by assaying a complex containing immunophilin, calcineurin, calmodulin, calcium ions and a calcineulin-inhibiting immunosuppressant.

According to the invention, it is possible to determine more accurately the total concentration of the substances actually having the immunosuppressant effect in the determination of the level of calcineulin-inhibiting immunosuppressants such as FK506 or cyclosporin A in blood.

3 Claims, No Drawings

SEQUENCE LISTING

```
<160> NUMBER OF SEQ ID NOS: 1

<210> SEQ ID NO 1
<211> LENGTH: 48
<212> TYPE: DNA
<213> ORGANISM: Artificial Sequence
<220> FEATURE:
<221> NAME/KEY: misc_feature
<223> OTHER INFORMATION: synthetic primer

<400> SEQUENCE: 1
ccacatgcca ctctcgtctt cgatgtggag cttctaaaac tggaatga                    48
```

METHOD FOR ASSAYING IMMUNOSUPPRESSANT

This application is a continuation of U.S. application Ser. No. 08/702,549, filed Oct. 24, 1996, now abandoned and a continuation of International Application No. PCT/JP95/00372, filed Mar. 8, 1995.

TECHNICAL FIELD

The present invention relates to a method of accurately assaying calcineurin-inhibiting immunosuppressants, such as FK506 and cyclosporin A, which method can be used in the field of medicine.

BACKGROUND ART

It is well known that a compound represented by the structural formula and chemical name shown below and also designated as FK506 or FR-900506 has potent immunosuppressive activity and can be used as a prophylactic or therapeutic agent for organ transplant rejection or autoimmune diseases (for example, EP-0184162-A2).

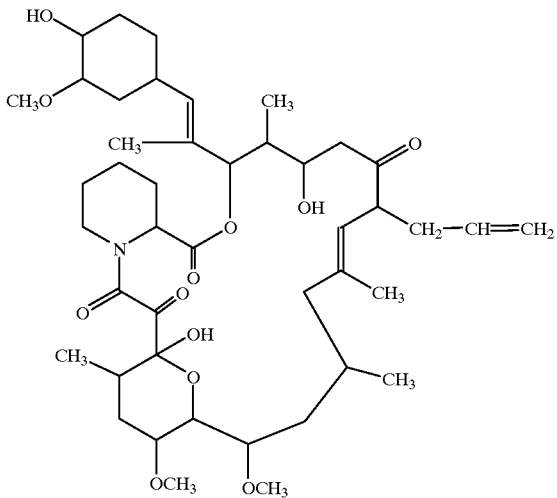

Chemical name: 17-Allyl-1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone As a result of investigations of the mechanism of immunosuppressive activity of FK506, said activity is supposed to be displayed as follows. FK506 binds to FKBP-12, which is a cytoplasmic FK506-binding protein, followed by association with calcineurin, together with calmodulin and calcium ion, to form a complex (FK506:FKBP-12: calcineurin= 1:1:1), whereby the phosphatase activity of calcineurin is inhibited. This phosphatase inhibition leads to suppression of the activation of nuclear factor of activated T cells (NFAT) and to inhibition of IL2 production, whereby immunosuppression is caused.

Cyclosporin A, which has similar immunosuppressive activity, is also supposed to show its immunosuppressive activity by forming a similar complex [cf. for example, Biochemical and Biophysical Research Communications, 192 (3), 1388–1394 (1993) and Angew. Chem., Int. Ed. Engl., 31 (1992) 384–400].

The utility of FK506 as an immunosuppressant has been amply studied and, in Japan, FK506 is already on the market as a rejection reaction suppressant particularly in liver transplantation.

However, since its activity is very potent, the determination of an optimum dose is an important issue. It is very important to administer it at a dose with displaying its effective immunosuppressive activity and without producing adverse effects or the like.

For that purpose, several assay methods have been proposed, including an enzyme immunoassay method with an antibody recognizing the antigenic determinant of FKS506 (e.g. EP-0293892-A2), a method in which the above-mentioned enzyme immunoassay is combined with HPLC, and a radioreceptor method utilizing an FK506-binding protein (FKBP-12) [cf. for example, Clin. Chem., 38/7, 1307–1310 (1992)].

On the other hand, studies on the mechanism of its metabolism have revealed that while FK506 undergoes metabolism in the living body, some of its metabolites still retain immunosuppressive activity, and others are capable of binding to a monoclonal antibody to FK506 with only weak immunosuppressive activity [e.g. Drug Metabolism and Disposition, 21 (6), 971–977 (1993)].

Furthermore, the existence of a substance (e.g. 506BD) capable of binding to FK506 binding proteins (FKBPs) but having no immunosuppressive activity has been revealed [e.g. Angew. Chem., Int. Ed. Engl., 31 (1992) 384–400].

Therefore, the previous assay methods using, as an index, either the binding of FK506 to an antibody recognizing the antigenic determinant of FK506, or the binding of an FKBP to FK506, can hardly be said to be capable of accurately measuring the actual state of immunosuppression. The development of an assay method capable of accurately measuring the total concentration of active drug substances including metabolites actually having immunosuppressive activity has been awaited.

DISCLOSURE OF THE INVENTION

Giving their attention to the fact that an immunosuppressant, such as FK506 or cyclosporin A, binds to an immunophilin (protein capable of binding to an immunosuppressant; e.g. FKBP-12 or cyclophilin) and then form a complex with calcineurin, calmodulin and calcium ion and thereby inhibits the activity of calcineurin, the inventors of the present invention succeeded in establishing a method of assaying immunosuppressants making use of the complex forming ability of said substances.

The present invention thus provides a method of assaying immunosuppressants having calcineurin-inhibiting activity, which comprises assaying a complex comprising (1) an immunophilin, (2) calcineurin, (3) calmodulin, (4) calcium ion and (5) an immunosuppressant having calcineurin-inhibiting activity.

In the following, the particular terms used herein within the scope of the present invention are defined and explained in detail and preferred examples are given.

The "immunophilin" means a cytoplasmic receptor protein to which an immunosuppressant binds and includes, for example, FKBP-12 which is an FK506 binding protein having a molecular weight of about 12K and peptidyl prolyl cis-trans isomerase (PPIase) activity, and cyclophilin which is an intracellular receptor for cyclosporin A and has similar PPIase activity and a molecular weight of about 17K. Preferred are FKBP-12 and cyclophilin produced by mammals such as cattle or humans.

They are already known and can be obtained in the same manner as described in J. Am. Chem. Soc., 113, 1409–1411 (1991), Proc. Natl. Acad. Sci. USA, 88, 6229–6233 (1991), Nature, 346, 671–674 (1991), WO 92/01052, WO 91/17439, Nature, 337, 473–475, 476–478 (1989), or Japanese Kokai Tokkyo Koho Hei 02-209897, for instance.

"Calcineurin" is known as a calcium ion- and calmodulin-dependent serine-threonine phosphatase, and calcineurin obtained from mammals such as rats, cattle or humans can be used. Rat or bovine calcineurin, for example, is known to be a heterodimer composed of A and B subunits and it is further known that the A subunit includes two isoforms, Aα and Aβ. Rat calcineurin can be isolated and purified, for example, from the rat brain [cf. for example, J. Neurochem., 58, 1643–1651 (1992)]. Bovine calcineurin can be obtained in the same manner as described in Adv. Enzymol., 61, 149–200 (1989) or Methods Enzymol., 102, 244–256 (1983). It is also commercially available from Upstate Biotechnology Co. Ltd or Sigma Co. Ltd under the product name "protein phosphatase 2B", for instance, and such product may also be used.

"Calmodulin" is a substance known as a calcium binding protein and is known to activate various enzymes including the above-mentioned calcineurin in the presence of the calcium ion. Calmodulin derived from mammals such as cattle or humans can be used. Bovine calmodulin, for instance, can be prepared and obtained as described in J. Biochem., 87, 1313–1320 (1980), and a commercial product available from Upstate Biotechnology Co. Ltd or Sigma Co. Ltd can also be used.

The "immunosuppressant having calcineurin-inhibiting activity" to be assayed in accordance with the present invention means a compound which inhibits the phosphatase activity of calcineurin by forming a complex with an immunophilin, calcineurin, calmodulin and calcium ion, and has immunosuppressive activity. Preferred examples are compounds of the following formula:

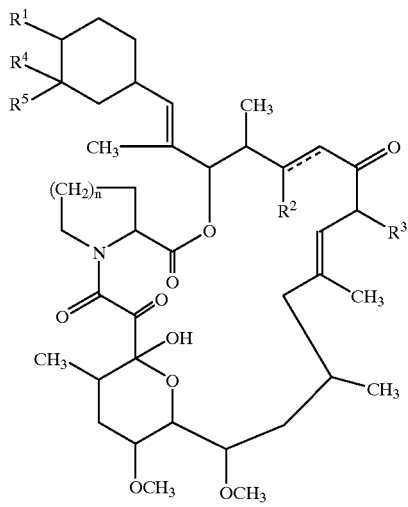

[I]

(wherein $R^1$ is hydroxy or protected hydroxy, $R^2$ is hydrogen, hydroxy or protected hydroxy, $R^3$ is methyl, ethyl, propyl or allyl, $R^4$ is hydroxy or methoxy, $R^5$ is hydrogen, or $R^4$ and $R^5$ together form oxo, n is an integer of 1 or 2, and the symbol comprising a solid line and a dotted line means a single bond or a double bond, provided that when $R^4$ is hydroxy and $R^5$ is hydrogen or when $R^4$ and $R^5$ together form oxo, $R^2$ is not protected hydroxy.)

The term "lower" as used in defining the symbols used in the above general formula [I], and in the subsequent description means, unless otherwise indicated, that the number of carbon atoms is 1 to 6.

Suitable protective groups for use in the "protected hydroxy" include the following: 1-(lower alkylthio) (lower) alkyl groups such as lower alkylthiomethyl (e.g. methylthiomethyl, ethylthiomethyl, propylthiomethyl, isopropylthiomethyl, butylthiomethyl, isobutylthiomethyl, hexylthiomethyl, etc.), and the like, more preferably $C_1$–$C_4$ alkylthiomethyl, most preferably methylthiomethyl; trisubstituted silyl groups such as tri (lower) alkylsilyl (e.g. trimethylsilyl, triethylsilyl, tributylsilyl, tert-butyl-dimethylsilyl, tri-tert-butylsilyl, etc.), lower alkyl-diarylsilyl (e.g. methyl-diphenylsilyl, ethyl-diphenylsilyl, propyl-diphenylsilyl, tert-butyl-diphenylsilyl, etc.), and the like, more preferably tri($C_1$–$C_4$)alkylsilyl and $C_1$–$C_4$ alkyldiphenylsilyl, most preferably tert-butyl-dimethylsilyl and tert-butyl-diphenylsilyl; acyl groups such as aliphatic acyl, aromatic acyl and aromatic group-substituted aliphatic acyl which are derived from carboxylic, sulfonic and carbamic acids; and the like.

As more specific examples of the above-mentioned acyl groups, there may be mentioned the following:

The aliphatic acyl may include lower alkanoyl which may have one or more suitable substituent(s) such as carboxy (e.g. formyl, acetyl, propionyl, butyryl, isobutyryl, valeryl, isovaleryl, pivaloyl, hexanoyl, carboxyacetyl, carboxypropionyl, carboxybutyryl, carboxyhexanoyl, etc.), cyclo (lower) alkoxy (lower) alkanoyl which may have one or more suitable substituent(s) such as lower alkyl (e.g. cyclopropyloxyacetyl, cyclobutyloxypropionyl, cycloheptyloxybutyryl, menthyloxyacetyl, menthyloxypropionyl, menthyloxybutyryl, menthyloxypentanoyl, menthyloxyhexanoyl, etc.), camphorsulfonyl, lower alkylcarbamoyl having one or more suitable substituent(s) such as carboxy or protected carboxy, for example carboxy(lower)alkylcarbamoyl (e.g. carboxymethylcarbamoyl, carboxyethylcarbamoyl, carboxypropylcarbamoyl, carboxybutylcarbamoyl, carboxypentylcarbamoyl, carboxyhexylcarbamoyl, etc.), protected carboxy(lower)alkylcarbamoyl such as tri(lower) alkylsilyl(lower)alkoxycarbonyl(lower)alkylcarbamoyl (e.g. trimethylsilylmethoxycarbonylethylcarbamoyl, trimethylsilylethoxycarbonylpropylcarbamoyl, triethylsilylethoxycarbonylpropylcarbamoyl, tert-butyldimethylsilylethoxycarbonylpropylcarbamoyl, trimethylsilylpropoxycarbonylbutylcarbamoyl, etc.), and the like.

The aromatic acyl may include aroyl which may have one or more suitable substituent(s) such as nitro (e.g. benzoyl, toluoyl, xyloyl, naphthoyl, nitrobenzoyl, dinitrobenzoyl, nitronaphthoyl, etc.), arenesulfonyl which may have one or more suitable substituent(s) such as halogen (e.g. benzenesulfonyl, toluenesulfonyl, xylenesulfonyl, naphthalenesulfonyl, fluorobenzenesulfonyl, chlorobenzenesulfonyl, bromobenzenesulfonyl, iodobenzenesulfonyl, etc.), and the like.

The aromatic group-substituted aliphatic acyl may include ar(lower)alkanoyl which may have one or more suitable substituent(s) such as lower alkoxy and trihalo (lower)alkyl (e.g. phenylacetyl, phenylpropionyl, phenylbutyryl, 2-trifluoromethyl-2-methoxy-2-phenylacetyl, 2-ethyl-2-trifluoromethyl-2-phenylacetyl, 2-trifluoromethyl-2-propoxy-2-phenylacetyl, etc.), and the like.

More preferred acyl groups among the above-mentioned acyl groups are $C_1$–$C_4$ alkanoyl which may have carboxy, cyclo($c_5$–$C_6$)alkyloxy($C_1$–$C_4$)alkanoyl having two ($C_1$–$C_4$) alkyl groups on the cycloalkyl moiety, camphorsulfonyl, carboxy($C_1$–$C_4$)alkylcarbamoyl, tri($C_1$–$C_4$)alkylsilyl ($C_1$–$C_4$)alkoxycarbonyl($C_1$–$C_4$)alkylcarbamoyl, benzoyl which may have one or two nitro groups, benzenesulfonyl having halogen, phenyl($C_1$–$C_4$)alkanoyl having $C_1$–$C_4$ alkoxy and trihalo($C_1$–$C_4$)alkyl. Most preferred among these are acetyl, carboxypropionyl, menthyloxyacetyl, camphorsulfonyl, benzoyl, nitrobenzoyl, dinitrobenzoyl, iodobenzenesulfonyl and 2-trifluoromethyl-2-methoxy-2-phenylacetyl, and the like.

The compounds represented by the above general formula [I] and a method of production thereof are already known, and said compounds may be obtained as similar manner to that of described in EP-0184162-A2 and EP-0353678-A2.

In particular, those compounds that are designated as FR900506 (=FK506), FR900520, FR900523 and FR900525 are produced by a microorganism of the genus Streptomyces, particularly *Streptomyces tsukubaensis* No. 9993 (FERM BP-927) or *Streptomyces hygroscopicus* subsp. *yakushimaensis* No. 7238 (FERM BP-928), as described in EP-0184162-A2.

Furthermore, cyclosporins, such as cyclosporin A, B, C, D, E, F and G, or derivatives thereof, which are already known as described, for example, in U.S. Pat. Nos. 4,117, 118, 4,215,199, 4,288,431 and 4,388,307, Helv. Chim. Acta, 60, 1568 (1977) and 65, 1655 (1982), and Transplant. Proc., 17, 1362 (1985), are also capable of complex formation with a cyclophilin, calcineurin, calmodulin and calcium ion and are therefore immunosuppressants having calcineurin-inhibiting activity, hence can be assayed by the assay method of the present invention.

The method of forming the complex comprising an immunophilin, calcineurin, calmodulin, calcium ion and an immunosuppressant having calcineurin-inhibiting activity in the practice of the present invention has no particular characteristic features and the complex can be formed by allowing a sample containing the immunosuppressant having calcineurin-inhibiting activity to react with an immunophilin, calcineurin, calmodulin and calcium ion in an appropriate solution in the conventional manner.

Thus, for example, it will suffice that the respective components be allowed to stand in an appropriate solution under warming at 30 to 40° C. for several hours.

In practicing said assay method actually in the field of medicine, the term "sample containing an immunosuppressant having calcineurin-inhibiting activity" means a whole blood or plasma sample obtained from a patient to whom the immunosuppressant having calcineurin-inhibiting activity has been administered. The sample is preferably subjected to SepPak column treatment as described in EP-0293892-A2, for instance, or pretreated with an extractant such as dichloromethane or methanol.

The complex obtained is separated by an appropriate method and then assayed in the conventional manner taking advantage of any component labeled with a radioisotope or enzyme or using an antibody recognizing some site of any of the components of the complex, whereby the target immunosuppressant can be quantified.

More specifically, the present invention can be practiced in such a manner as mentioned below. Hereinafter, the "immunosuppressant having calcineurin-inhibiting activity" is referred to "immunosuppressant" for short. (1) One of the complex-constituting components, appropriately selected, is fixed or bound to a solid phase such as a plate, test tube, bead or the like in the conventional manner so that the complex obtained can remain fixed to the solid phase. This makes it easy to remove the reaction mixture containing unnecessary components etc. after complex formation.

The complex-constituting component which is to be appropriately selected for binding to the solid phase is the immunophilin, calcineurin or calmodulin.

(1-1): Thus, for example, an excessive amount of an immunophilin fixed to a solid phase, and calmodulin, calcium ion and calcineurin, each in an excessive amount, are reacted with the assay target immunosuppressant contained in the sample, whereby a complex is formed in an amount corresponding to the immunosuppressant content. The complex is separated by suction of the reaction mixture and washing with an appropriate buffer solution, for instance. Then, the complex, hence the complex-forming immunosuppressant, can be assayed using an appropriate enzyme-labeled antibody which recognizes calcineurin or calmodulin.

As the "enzyme-labeled antibody which recognizes calcineurin or calmodulin", there may be mentioned an anti-calcineurin antibody or anti-calmodulin antibody bound, in the conventional manner, to an enzyme generally used in enzyme immunoassay (e.g. peroxidase, β-D-galactosidase, alkaline phosphatase, glucose oxidase, acetylcholine esterase, glucose-6-phosphate dehydrogenase, malate dehydrogenase, urease, etc.).

The complex recognized by such an enzyme-labeled antibody as mentioned above can be quantified by assaying the enzyme activity of the label enzyme by the conventional method described in EP-0293892-A2, for instance. Thus, when the label enzyme is peroxidase, for instance, an enzyme substrate solution containing o-phenylenediamine and hydrogen peroxide is used and the color intensity is measured, whereby the complex can be assayed. When the enzyme is alkaline phosphatase, 4-methylumbelliferyl phosphate is used as the enzyme substrate.

(1-2): It is also possible to use, in lieu of the "enzyme-labeled antibody recognizing calcineurin or calmodulin", an antibody recognizing calcineurin or calmodulin (first antibody) and an enzyme-labeled antibody-recognizing said first antibody (second antibody).

As the anti-calcineurin or anti-calmodulin antibody to be used in assay method (1-1) usable as the above first antibody, there is a polyclonal antibody or a monoclonal antibody prepared in the conventional manner using calcineurin or calmodulin as an antigen [e.g. J. Neurochem., 58 (5), 1643–1651 (1992)]. It is possible, however, to use a commercially available anti-calcineurin antibody (=anti-protein phosphatase 2B) or anti-bovine calmodulin antibody marketed by Upstate Biotechnology Co. Ltd. While the class of the antibody is not limited to any particular one, the IgG class is preferred and an antibody obtained by immunization of mice or the like can be used.

Any polyclonal or monoclonal antibody capable of recognizing the first antibody can be used as the second antibody mentioned above, with such an enzyme as mentioned above under (1-1) bound thereto in the conventional manner. For instance, alkaline phosphatase-labeled anti-rabbit IgG is commercially available and can be purchased, for example, from Vector Laboratories (USA), and it can be used as the labeled second antibody.

(1-3): It is further possible to quantify the complex formed corresponding to the quantity of the immunosuppressant present in the sample, in the conventional manner with enzyme activity or radioactivity as an index, by using, in lieu of ordinary calcineurin or calmodulin, calcineurin or calmodulin labeled by a conventional method with an appropriate enzyme such as mentioned above or an radioisotope (e.g. $^{125}$I), in the step of causing complex formation as mentioned under (1-1) following excess immunophilin binding to a solid phase.

(1-4): Calcineurin or calmodulin, each in excess, may be first fixed to a solid phase, in lieu of the immunophilin. In that case, the immunophilin and calcium ion, each in excess, and the sample are added, and complex formation and separation are effected in the same manner as mentioned above. Then, the complex can be assayed using an "antibody labeled with an appropriate enzyme and capable of recognizing the immunophilin" (enzyme-labeled anti-immunophilin antibody) prepared by a conventional method. Alternatively, a first antibody recognizing the immunophilin and an enzyme-labeled second antibody capable of recognizing said first antibody may be used as mentioned under (1-2).

(2) On the other hand, it is possible to separate and recover the complex formed, without immobilizing any of the complex-forming components. Thus, the complex formed can be precipitated and separated by reacting therewith an antibody capable of recognizing one of the complex-forming components.

(2-1): For example, the complex can be precipitated and separated using an antibody recognizing calcineurin or calmodulin. In that case, the assay is possible when a certain definite amount of the immunosuppressant labeled with a radioisotope such as $^3$H is caused to be simultaneously present.

(2-2): On the other hand, the complex can be precipitated and separated using a polyclonal or monoclonal antibody, which recognizes the immunophiline, prepared as described, for example, in International Patent Application WO 94/04700. In that case, calcineurin or calmodulin to be used for complex formation is labeled with an appropriate enzyme or radioisotope (e.g. $^{125}$I) as in the case of (1-3) so that the complex can be assayed by a conventional method.

Said-appropriate enzyme to be used for labeling in the above methods (2-2), (1-3) and (1-4) may be any of those described under (1-1).

While various assay methods are conceivable as mentioned above, a preferred quantitive method of immunosuppressant comprises reacting the immunophilin bound in excess to a solid phase with calcineurin, calmodulin and calcium ion, each in excess as well as the immunosuppressant in the sample to thereby cause formation of a complex in an amount corresponding to the amount of the immunosuppressant and, after separation treatment, assaying the calcineurin constituting the thus-obtained complex by an enzyme immunoassay technique. In that case, the enzyme immunoassay technique is preferably one using an anti-calcineurin antibody labeled with an enzyme in standard use, such as peroxidase or alkaline phosphatase, or one using two antibodies, namely an anti-calcineurin antibody and an anti-IgG antibody labeled with such an enzyme as mentioned above.

The assay method of the present invention can be practiced by using either automatic or nonautomatic (manual) means.

Furthermore, a convenient kit can be provided for practicing said assay method. The kit may include all or some of an immunophilin, calcium ion, calmodulin, calcineurin and the immunosuppressant as a standard. It may further include, when necessary, the immunosuppressant labeled with a radioisotope, calcineurin or calmodulin labeled with an appropriate enzyme or radioisotope, an anti-immunophilin, anti-calcineurin or anti-calmodulin antibody labeled with an appropriate enzyme, an anti-immunophilin antibody, an anti-calcineurin antibody, an anti-calmodulin antibody, and/or the like.

On the occasion of complex formation, the calcium ion is used in ordinary cases. However, it is also possible to use any other ion if it can participate in complex formation together with calcineurin, calmodulin and the immunosuppressant. Thus, for instance, the manganese ion, which contributes to similar complex formation as established in Biochemical and Biophysical Research Communications, 192 (3), 1388–1394 (1993), can be used as an alternative.

Furthermore, the complex comprising an immunophilin, calcineurin, calmodulin, calcium ion and the immunosuppressant having calcineurin-inhibiting activity may further have any other component(s) added or attached thereto provided that said components will not disturb the separation and assay following complex formation.

The following examples are illustrative of the present invention.

Preparation 1 Production of FKBP-12

Based on the DNA sequence reported by S. L. Schreiber et al. of Harvard University in Nature, 346, 671–674 (1990), a DNA 48-mer corresponding to the C terminal of FKBP-12 was synthesized using a DNA synthesizer (Applied Biosystems Co. Ltd).

5'-CCACATGCCACTTCGTCTTCGATGTGGAGCTTC TAAAACTGGAATGA-3' (SEQ. ID NO: 1)

The terminal of This 48-mer was labeled with $^{25}$P and was used the same as a probe. A human T cell cDNA library HL1016b, 500,000 plaques, was screened, whereby one positive plaque was obtained. From this plaque, a fragment containing FKBP-12 cDNA was subcloned [pUC-23(Ec)]. Sequencing of this pUC-23(Ec) revealed deletion of the 1st to 32nd nucleotides, corresponding to the N terminal, of the DNA sequence. After making up for the deficient portion, the subclone, together with an about 80 b.p. AT rich silent mutant N-terminal DNA synthesized for enhancing the expression in *Escherichia coli,* was inserted, as an EcoRI-BamHI site insert, into a plasmid, capable of gene expression under the control of the tryptophan promoter, prepared as described in J. Biochem., 101, 123–134 (1987), whereby an expression vector, pFKBP333, was obtained. Using this vector, *E. coli* HB101 was transfered to give an expression cell line, HB101/pFKBP(AT)311. The cell was incubated in L-amp. broth for 19 hours and protein synthesis was induced by the addition of IAA (indoleacrylic acid) to a final concentration of 90 $\mu$/ml. *E. coli* cells were harvested and disrupted with a French Press in 50 mM Tris-HCl, 2 mM β-ME, 2 mM CaCl$_2$, 10 mM MgCl$_2$ and 5% glycerol, followed by centrifugation (4° C., 6,000×g, 30 minutes). The supernatant was heat-treated at 60° C. for 15 minutes and then centrifuged (4° C., 6,000×g, 45 minutes+4° C., 18,000× g, 20 minutes×2 times), dialyzed [20 mM Tris-HCl (pH 7.4), 4° C., overnight] and subjected to DEAE-Toyo Pearl 650 M reversed phase HPLC (C4), to thereby purify FKBP-12.

Using the thus-purified FKBP-12 and a calcium ion-and magnesium ion-free phosphate buffer solution having the composition shown below, FKBP-12 in a phosphate-buffered solution (50 $\mu$/ml) was prepared.

| Phosphate buffer (pH 7.4) composition | |
|---|---|
| Sodium chloride | 8.0 g |
| Potassium chloride | 0.2 g |
| Disodium hydrogen phosphate, anhydrous (Na$_2$HPO$_4$) | 1.15 g |
| Potassium dihydrogen phosphate, anhydrous (KH$_2$PO$_4$) | 0.2 g |
| Add distilled water to make 1,000 ml. | |

EXAMPLE 1

Method of Assaying FK506

(1) One hundred microliter FKBP-12 in the phosphate-buffered solution (50 $\mu$/ml) obtained as described in Preparation 1 was added into each well of an immuno microtiter plate and shaken overnight at 40° C. The plate was then washed 3 times with the same phosphate buffer solution as used in Preparation 1. FKBP-12 was thus bound to each well. An assay buffer (300 $\mu$l) having the composition shown below was added to each well and, after 15 minutes, it was removed, to block residual protein binding sites in each well.

| Assay buffer composition | |
|---|---|
| Tris hydrochloride | (50 mM, pH 7.5) |
| Bovine serum albumin | (5 mg/ml) |
| Triton | (0.001%) |
| DTT | (0.5 mM) |
| Calcium chloride | (1 mM) |

(2) Then, a crude bovine calcineurin solution (50 $\mu$l), a bovine calmodulin solution (50 $\mu$l) and an FK506 solution (100 µl), each in a dilution form, prepared as described below, were respectively added to each well, and the plate was allowed to stand at 37° C. for 1 hour, for allowing complex formation.

Crude Bovine Calcineurin Solution

A solution (5 mg/ml) of a crude product, prepared by the conventional method, in 20 mM Tris-hydrochloride (pH 7.0) was 40-fold diluted with the above-mentioned assay buffer.

Bovine Calmodulin Solution

Commercial bovine calmodulin was appropriately diluted with the above-mentioned assay buffer (to give a final concentration of 95 nM in the well).

FK506 Solution

A methanol solution (1 mg/ml) of FK506 was appropriately diluted with the above-mentioned assay buffer.

(3) Each well was washed (4 times) with the same buffer as the above-mentioned assay buffer except that it was free of bovine serum albumin and, then, an appropriate dilution (100 µl), in the assay buffer, of a rabbit polyclonal antibody recognizing the calcineurin Aα chain as obtained by the known method described, for example, in J. Neurochem., 58, 1643–1651 (1992) was added to each well, and the reaction was allowed to proceed at room temperature for 1 hour.

(4) Each well was washed (4 times) with the same buffer as the above-mentioned assay buffer except that it was free of bovine serum albumin and, then, an appropriate dilution (100 µl), in the assay buffer, of alkaline phosphatase-labeled anti-rabbit IgG (Vector Laboratories) was added to each well.

(5) Each well was washed (4 times) with the same buffer as the assay buffer except that it was free of bovine serum albumin and, then, 200 µl of a 4-methylumbelliferyl phosphate (hereinafter, 4-MU) substrate solution (1 mM), prepared as described below, was added to each well and, after the lapse of 20 minutes at room temperature, fluorometry (excitation wavelength 360 nm; emission wavelength 460 nm) was carried out using Cytofluor 2350 (trademark, Millipore Co. Ltd, USA). The results obtained are shown in Table 1.

4-MU Substrate Solution

A 100 mM solution of 4-MU (Sigma Co. Ltd) was prepared with water and further diluted with a buffer solution (10 mM, pH 10.0) comprising diethanolamine (0.7 ml/l) and magnesium chloride hexahydrate (0.1 g/l) to give a 1 mM 4-MU substrate solution.

EXAMPLE 2

Method of Assaying FK506 Metabolites

Using the metabolites M-II and M-III shown below, which are already known as metabolites obtainable upon treatment of FK506 with rat liver microsome, as described, for example, in Drug Metabolism and Disposition, 21 (6), 971–977, quantitative analysis was carried out in the same manner as in Example 1.

The results obtained are shown in Table 1.

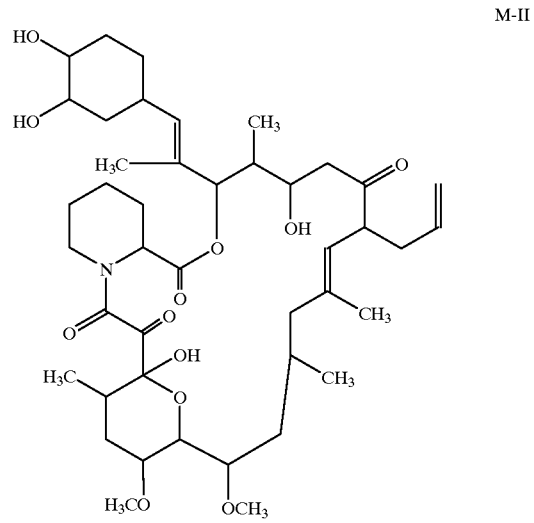

M-II

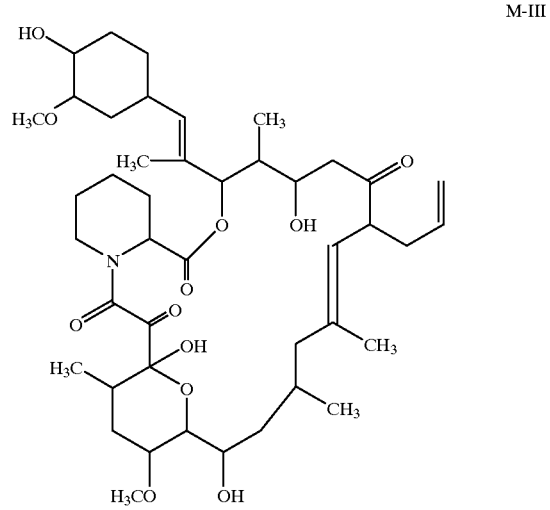

M-III

TABLE 1

Assay of FK506 and its metabolites

| Conc. of FK506 or its metabolite | Fluorescence intensity (mean ± standard deviation) n = 3 | | |
|---|---|---|---|
| (ng/nl) | FK506 | M-II | M-III |
| 0 | 762.8 ± 192.3 | 885.3 ± 34.6 | 948.3 ± 16.3 |
| 3.9 | 1302.3 ± 4.9 | 1318.8 ± 9.9 | 962.3 ± 12.0 |
| 7.8 | 1591.3 ± 41.7 | 1639.8 ± 36.8 | 967.8 ± 43.8 |
| 15.6 | 1933.3 ± 112.4 | 1883.3 ± 98.3 | 936.8 ± 0.0 |
| 31.3 | 2131.3 ± 119.5 | 2188.8 ± 0.0 | 892.8 ± 134.4 |
| 62.5 | 2753.8 ± 67.9 | 2472.3 ± 55.9 | 1033.3 ± 16.3 |
| 125 | 2967.3 ± 47.4 | 2701.8 ± 96.2 | 1147.8 ± 193.7 |
| 250 | 3148.3 ± 224.2 | 2867.3 ± 30.4 | 1034.8 ± 99.0 |
| 500 | 3392.8 ± 0.0 | 3040.8 ± 24.0 | 978.8 ± 4.2 |
| 1000 | 3519.8 ± 17.7 | 3192.8 ± 8.5 | 1150.3 ± 55.9 |

The results shown in Table 1 indicate that FK506 and M-II give fluorescence intensities depending on their concentrations, while M-III does not give concentration-dependent values.

EXAMPLE 3

To confirm that the blood concentrations of FK506 and metabolites thereof that are not only capable of binding to FKBP-12 but also actually show immunosuppressive activity can alone be determined, FK506 and its metabolites mentioned previously (M-II and M-III) were evaluated for FKBP-12 binding activity and immunosuppressive activity, as follows.

(1) The FKBP-12 binding activity measurement was carried out in the same manner as described in Clinical Chemistry, 38/7, 1307–1310 (1992), using $^3$H-dihydro-FK506, FKBP-12, dextran charcoaled, etc.

(2) The immunosuppressive activity was measured by the well-known in vitro mixed lymphocyte reaction (MLR) test described, for example, in European Patent Application EP-0184162-A2, page 67. The results obtained are shown in Table 2.

TABLE 2

|  | FKBP-12 binding activity (relative %) | Immunosuppressive activity (MLR) (relative %) | Complex forming activity (relative %) |
| --- | --- | --- | --- |
| FK506 | 100 | 100 | 100 |
| M-II | 14.2 | 100 | 79.7 |
| M-III | 116.0 | 0 | 0 |

The relative complex formation activity values shown In Table 2, were calculated based on the data shown in Table 1.

From the results shown in Table 2, it was confirmed that such a metabolite as M-III that has FKBP-12 binding activity but has no immunosuppressive activity is not detected by said complex assay method (i.e. the relative complex forming activity (%) being 0), but only those substances that have immunosuppressive activity, such as FK506 and its active metabolite (M-II), can be detected.

EXAMPLE 4

Method of Assaying Cyclosporin A (1) Human cyclophilin purchased from Sigma Co. Ltd was bound, in lieu of FKBP-12, to each well in the same manner as in Example 1 (1).

(2) Then, the same crude bovine calcineurin solution and bovine calmodulin solution as used in Example 1 (2) and the following cyclosporin A solution were reacted with each well, for causing complex formation.

Cyclosporin A Solution

A solution (1 mg/ml) of cyclosporin A in methanol was appropriately diluted-with the same assay buffer as used in Example 1 (1).

(3) After washing with the bovine serum albumin-free assay buffer prepared as in Example 1 (3), a solution (1 μg/ml) of a mouse monoclonal antibody to the β subunit of calcineurin (α-CN β-MoAb), which is purchased from Upstate Biotechnology Co. Ltd, as prepared by diluting with the above-mentioned assay buffer was distributed in 100 μl portions into the wells. The reaction was then conducted for 1 hour.

Thereafter, fluorometry was performed in the same manner as in Example 1 (4) and (5), and the complex formed for each concentration of cyclosporin A was quantified. The results obtained are shown in Table 3.

TABLE 3

| Assay of cyclosporin A | |
| --- | --- |
| Concentration of cyclosporin A (ng/ml) | Fluorescence intensity |
| 0 | 289 |
| 15.6 | 470 |
| 31.3 | 540 |
| 62.5 | 672 |
| 125 | 948 |
| 250 | 1297 |
| 500 | 1613 |
| 1000 | 2060 |
| 2000 | 2207 |
| 4000 | 2408 |

The use of the assay method according to the invention has made it possible to accurately determine the blood level of an immunosuppressant having calcineurin-inhibiting activity, particularly compound [I], typically FK506, following administration thereof for therapeutic or prophylactic purposes to patients with symptoms or diseases, such as mentioned below, for instance.

Rejection in transplantation of an organ or tissue, such as heart, kidney, liver, bone marrow, skin, cornea, lung, pancreas, small intestine, limb, muscle, nerve, intervertebral disk or trachea; graft-versus-host reaction following bone marrow transplantation; autoimmune diseases such as rheumatoid arthritis, systemic lupus erythematosus, Hashimoto's thyroiditis, multiple sclerosis, myasthenia gravis, primary mucosal edema, autoimmune atrophic gastritis, premature menopause, male sterility, juvenile diabetes mellitus, pemphigus vulgaris, pemphigoid, sympathetic ophthalmitis, lens-induced uveitis, idiopathic leukopenia, active chronic hepatitis, idiopathic cirrhosis, discoid lupus erythematosus, type I diabetes, etc.; infectious diseases caused by pathogenic microorganisms (e.g. *Aspergillus fumigatus, Fusarium oxysporum, Trichophyton asteroides*, etc.);

inflammatory and hyperproliferative skin diseases and cutaneous manifestations of immunologically mediated illnesses (e.g. psoriasis, atopic dermatitis, contact dermatitis, eczematous dermatitis, seborrheic dermatitis, lichen planus, pemphigus, bullous pemphigoid, epidermolysis bullosa, urticaria, angioedema, vasculitis, erythema, cutaneous eosinophilia, lupus erythematosus, acne and alopecia areata);

autoimmune eye diseases (e.g. keratoconjunctivitis, vernal conjunctivitis, Behcet's disease-associated uveitis, keratitis, herpetic keratitis, conical keratitis, dystrophia epithelialis corneae, corneal leukoma, ocular pemphigus, Mooren's ulcer, scleritis, Graves' ophthalmopathy, Vogt-Koyanagi-Harada syndrome, sarcoidosis, etc.);

reversible obstructive airway diseases [asthma (e.g. bronchial asthma, allergic asthma, intrinsic asthma, extrinsic asthma and dust asthma), particularly chronic or inveterate asthma (e.g. late asthma and airway hyper-responsiveness), bronchitis, etc.];

inflammation of mucosa and blood vessels (e.g. gastric ulcer, vascular injury caused by ischemic diseases and thrombosis, ischemic bowel diseases, enteritis, necrotizing enterocolitis, intestinal lesions associated with thermal burns, leukotriene $B_4$-associated diseases);

intestinal inflammations/allergies (e.g. celiac disease, proctitis, eosinophilic gastroenteritis, mastocytosis, Crohn's disease and ulcerative colitis);

food-related allergic diseases which have symptomatic manifestation remote from the gastrointestinal tract (e.g. migraine, rhinitis and eczema);

renal diseases (e.g. interstitial nephritis, Goodpasture's syndrome, hemolytic-uremic syndrome and diabetic nephropathy);

nervous diseases (e.g. multiple myositis, Guillain-Barré syndrome, Ménière's disease, multiple neuritis, mononeuritis and radiculopathy);

endocrine diseases (e.g. hyperthyroidism and Basedow's disease);

hematic diseases (e.g. pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia); bone diseases (e.g. osteoporosis);

respiratory diseases (e.g. sarcoidosis, pulmonary fibrosis and idiopathic interstitial pneumonia);

skin diseases (e.g. dermatomyositis, leukoderma vulgaris, ichthyosis vulgaris, hypersensitivity to light, and cutaneous T cell lymphoma);

circulatory diseases (e.g. arteriosclerosis, atherosclerosis, aortitis syndrome, polyarteritis nodosa and myocardosis);

collagen diseases (e.g. scleroderma, Wegener's granuloma and Sjögren's syndrome);

adiposis;

eosinophilic fasciitis;

periodontal diseases [e.g. lesions of gingiva, periodontium, alveolar bone, substantia ossea (of teeth) ];

nephrotic syndrome (e.g. glomerulonephritis);

male pattern alopecia or alopecia senilis;

muscular dystrophy;

pyoderma and Sézary's syndrome;

Addison's disease;

chromosome abnormality-associated diseases (e.g. Down's syndrome);

active oxygen-mediated diseases [e.g. organ injury (ischemia-reperfusion injury of organs (e.g. heart, liver, kidney, digestive tract, etc.) which occurs on preservation, transplantation or ischemic diseases (e.g. thrombosis, cardiac infarction, etc.));

intestinal diseases (e.g. endotoxin shock, pseudomembranous colitis, drug- or radiation-induced colitis); renal diseases (e.g. ischemic acute renal insufficiency, chronic renal insufficiency); pulmonary diseases [e.g. toxicosis caused by lung oxygen or a drug (e.g. paracort, bleomycins), lung cancer, pulmonary emphysema]; ocular diseases (e.g. cataracta, siderosis, retinitis, pigmentation, senile macular degeneration, vitreous scarring, corneal alkali burn);

dermatitis (e.g. erythema multiforme, linear immunoglobulin A dermatitis, cement dermatitis); and other diseases [e.g. gingivitis, periodontitis, sepsis, pancreatitis, or diseases caused by environmental pollution (e.g. air pollution), aging, carcinogens, cancerous metastasis or hypobaropathy]];

diseases caused by histamine or leukotriene $C_4$ release;

Behcet's syndrome (e.g. intestinal, vascular, neuro, oral, cutaneous, ocular, vulval, articular, epididymal, pulmonary, renal);

hepatic diseases [e.g. immunogenic diseases (e.g. autoimmune hepatic diseases, primary biliary cirrhosis, sclerosing cholangitis, other chronic autoimmune liver diseases), partial liver resection, acute liver necrosis (e.g. necrosis caused by toxins, viral hepatitis, shock or anoxia), hepatitis b, hepatitis non-A/non-B, cirrhosis (e.g. alcoholic cirrhosis) and hepatic failure (e.g. fulminant hepatitis, late-onset hepatitis and acute-on-chronic liver failure)].

What is claimed:

1. A method of assaying immunosuppressants having calcineurin-inhibiting activity, which comprises causing formation of a complex comprising (1) FKBP-12 bound to a solid phase, (2) calcineurin, (3) calmodulin, (4) calcium ion and (5) an immunosuppressant having calcineurin-inhibiting activity; and assaying said complex with an enzyme immunoassay which detects calcineurin, wherein said assaying comprises adding a anti-calcineurin antibody which recognizes the calcineuring Aα-chain followed by adding an alkaline phosphatase labeled anti-IgG antibody which recognizes said anti-calcineurin antibody.

2. The-assay method of claim 1, wherein the immunophilin is FKBP-12 and the immunosuppressant having calcineurin-inhibiting activity is a compound (I) represented by the following general formula:

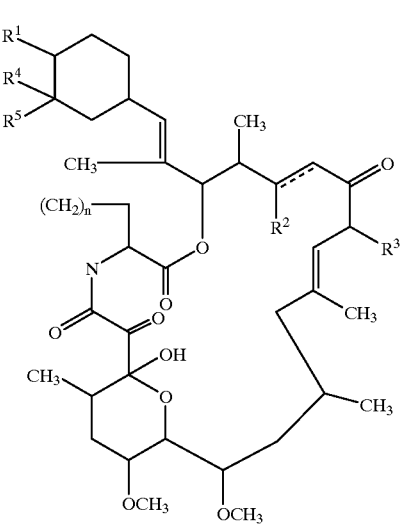

wherein $R^1$ is hydroxy or protected hydroxy, $R^2$ is hydrogen, hydroxy or protected hydroxy, $R^3$ is methyl, ethyl, propyl or allyl, $R^4$ is hydroxy or methoxy, $R^5$ is hydrogen, or $R^4$ and $R^5$ together form oxo, n is an integer of 1 or 2, the symbol comprising a solid line and a dotted line means a single bond or a double bond, provided that when $R^4$ is hydroxy and $R^5$ is hydrogen or when $R^4$ and $R^5$ together form oxo, $R^2$ is not protected hydroxy.

3. The assay method of claim 2, wherein the compound (I) is 17-allyl-1,14-dihydroxy-12-[2-(-hydoxy-3-methoxycyclohexyl)-1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone.

* * * * *